United States Patent
Tupper

(10) Patent No.: US 8,372,107 B2
(45) Date of Patent: Feb. 12, 2013

(54) DILATORS

(75) Inventor: Stephen Mark Tupper, Hythe (GB)

(73) Assignee: Smiths Group PLC, London (GB)

( * ) Notice: Subject to any disclaimer, the term of this patent is extended or adjusted under 35 U.S.C. 154(b) by 686 days.

(21) Appl. No.: 12/308,565

(22) PCT Filed: Jul. 19, 2007

(86) PCT No.: PCT/GB2007/002738
§ 371 (c)(1),
(2), (4) Date: Dec. 18, 2008

(87) PCT Pub. No.: WO2008/009943
PCT Pub. Date: Jan. 24, 2008

(65) Prior Publication Data
US 2009/0312784 A1    Dec. 17, 2009

(30) Foreign Application Priority Data
Jul. 21, 2006 (GB) .................................. 0614507.2

(51) Int. Cl.
*A61M 29/00* (2006.01)
(52) U.S. Cl. ....................................... 606/191
(58) Field of Classification Search .......... 606/190–199; 604/164.09, 164.1, 164.11, 164.13, 103.04; 128/207.14
See application file for complete search history.

(56) References Cited

U.S. PATENT DOCUMENTS

| | | | | |
|---|---|---|---|---|
| 672,377 A | * | 4/1901 | Kearns ........................ | 606/191 |
| 3,704,712 A | * | 12/1972 | Giesy et al. .................. | 606/198 |
| 3,908,637 A | * | 9/1975 | Doroshow .................... | 600/573 |
| 4,363,391 A | | 12/1982 | Langen | |
| 4,535,759 A | * | 8/1985 | Polk et al. .................... | 601/2 |
| 4,898,163 A | | 2/1990 | George | |
| 5,074,846 A | * | 12/1991 | Clegg et al. ................ | 604/164.1 |
| 5,380,290 A | * | 1/1995 | Makower et al. ........ | 604/164.01 |
| 5,496,344 A | * | 3/1996 | Kanesaka et al. ............. | 606/191 |
| 5,653,230 A | | 8/1997 | Ciaglia et al. | |
| 5,690,669 A | * | 11/1997 | Sauer et al. .................. | 606/196 |
| 6,637,435 B2 | | 10/2003 | Ciaglia | |
| 2004/0087991 A1 | | 5/2004 | Woo | |
| 2006/0100657 A2 | | 5/2006 | Ciaglia | |

FOREIGN PATENT DOCUMENTS

| | | |
|---|---|---|
| DE | 10065604 | 7/2001 |
| EP | 1281414 | 2/2003 |
| GB | 2394669 | 12/2005 |
| WO | 2005/094926 | 10/2005 |

* cited by examiner

*Primary Examiner* — Elizabeth Houston
(74) *Attorney, Agent, or Firm* — Louis Woo

(57) ABSTRACT

A tracheostomy dilator is curved along its length having a tapering patient end region (5) at one end and an oppositely curved handle region (7) at its opposite end. A passage (10) extends rearwardly along the dilator from its patient end (4) and opens on a side of the dilator at an opening (12) in the handle region (7). The passage (10) is blocked rearwardly of the opening (12) by an insert (2) with a forward ramp surface (23), which directs a guidewire (30). In use, one end of the guidewire (30) projects from the patient end (4) of the dilator and its opposite end extends along the outside of the handle region (7).

5 Claims, 2 Drawing Sheets

DILATORS

This invention relates to tracheostomy dilators of the kind comprising a curved, tapered patient end region adapted for insertion through a tracheostomy to expand the tracheostomy, a handle region towards the rear end of the dilator opposite the patient end region and a passage for receiving a guide member extending within the dilator from its patient end.

Percutaneous tracheostomies can be formed in various ways. One technique involves the steps of inserting a hollow needle through the skin into the trachea, inserting a guidewire along the needle, withdrawing the needle over the guidewire and then using one or more dilators slid along the guidewire to expand the opening sufficiently to enable a tracheostomy tube to be inserted. Where a series of several dilators are used these have an increasing diameter so that the opening is gradually expanded. Alternatively, a single, more steeply tapered dilator can be used, as described in, for example U.S. Pat. No. 4,364,391, DE 10065604, U.S. Pat. No. 4,898,163, U.S. Pat. No. 6,637,435, US2006/0100657 and GB2394669. The use of a single dilator is an advantage because it reduces the number of steps in the procedure and the number of components. Previous dilators have a passage extending along their length within which the guidewire or catheter is slidably received. Some users prefer to insert the guidewire to the trachea with the dilator loaded on it so that both the guidewire and dilator are inserted together. With conventional dilators it can be difficult to grip both the guidewire and dilator simultaneously.

It is an object of the present invention to provide an alternative dilator.

According to one aspect of the present invention there is provided a tracheostomy dilator of the above-specified kind, characterised in that the passage opens on a side of the dilator through an opening forwardly of its rear end.

The passage preferably opens within the handle region. The handle region is preferably curved in an opposite sense from the patient end region, forming a smooth continuous curve with the patient end region. The passage preferably opens on an inside curve of the handle region. The handle region may include an insert with a ramp surface arranged to direct a guide member inserted in the dilator.

According to another aspect of the present invention there is provided an assembly of a dilator according to the above one aspect of the invention and a guide member, characterised in that one end of the guide member projects from the patient end of the dilator, and that a part of the guide member emerging from the opening of the passage of the dilator extends rearwardly along the outside of the handle region.

A dilator according to the present invention will now be described, by way of example, with reference to the accompanying drawings, in which.

Figure 1:
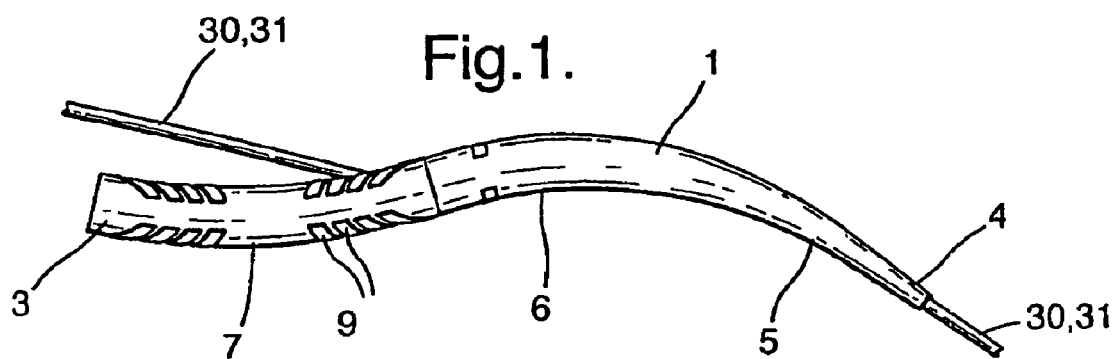
FIG. 1 is a side elevation view of the dilator showing a guidewire extending along the dilator.
Figure 2:
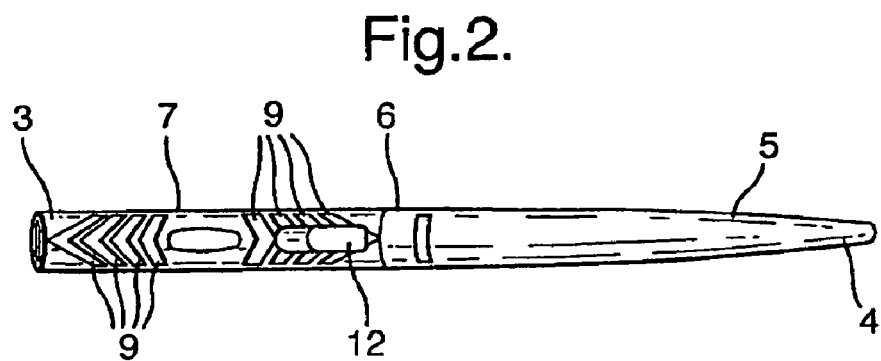
FIG. 2 is a plan view of the dilator without the guidewire.
Figure 3:
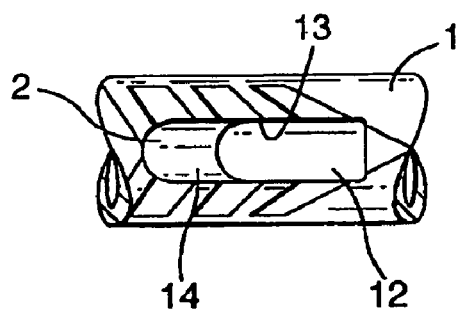
FIG. 3 is an enlarged plan view of a part of the dilator in the region of the rear end opening of the passageway.
Figure 4:
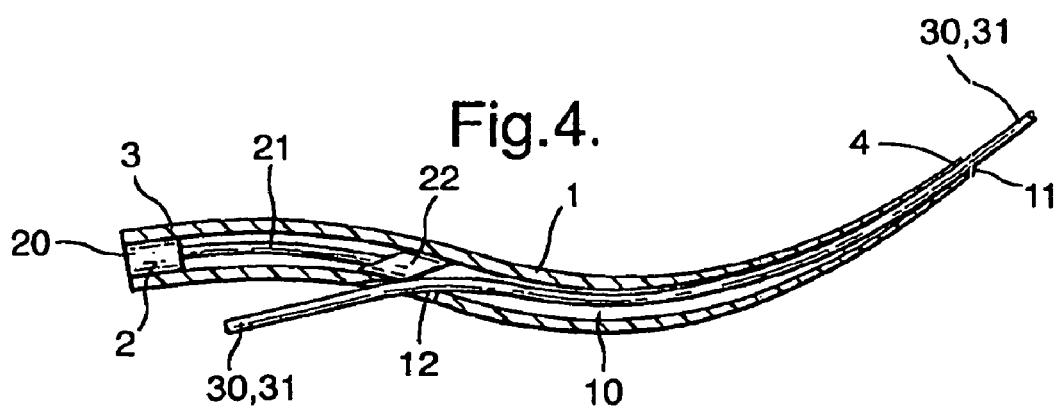
Figure 5:
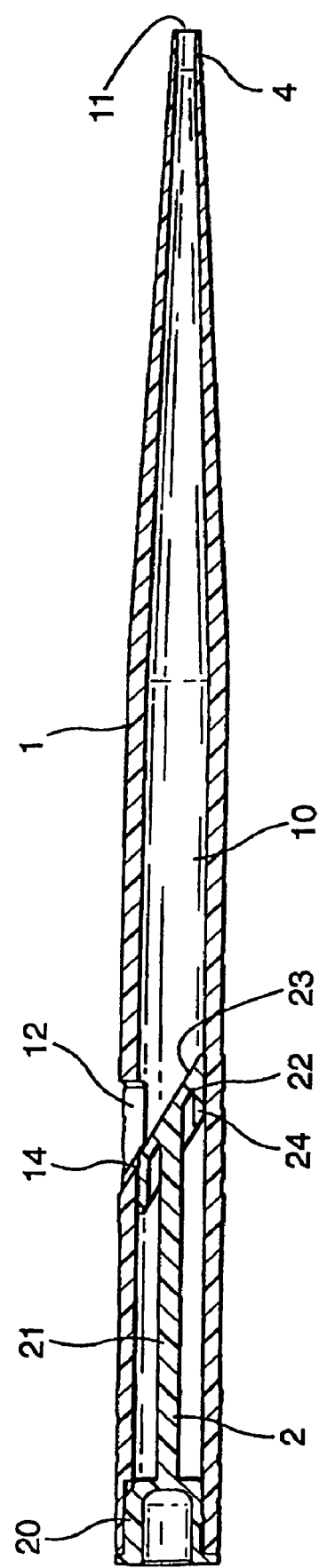

FIG. 4 is a cross-sectional side elevation view of the dilator with the guidewire: and FIG. 5 is a cross-sectional side elevation view of the dilator before being bent The dilator comprises an outer, tubular component 1 and a rod-like component or plug or insert 2 inserted in the rear of the dilator. The tubular component 1 is a single piece, integral moulding of a stiff but flexible plastics material, such as polyurethane with a Shore hardness of 90 A. The overall length of the dilator is 200 mm and it has a circular section along its length, with a diameter of 13.65 mm at its rear end 3 and a diameter of 4.0 mm at the tip 4 of its forward or patient end.

The dilator has three regions along its length: a patient end or forward region 5, an intermediate region 6 and a handle or rear region 7.

The patient end region 5 extends for 80 mm and tapers along its entire length from a diameter of 4 mm at the tip 4 to a diameter of 12.85 mm or 38 FR at the rear end of the region. The intermediate region 6 extends for 40 mm and has a constant diameter along its length. The handle region 7 extends for 80 mm and is also of constant diameter along its length. The tubular component 1 is moulded in the handle region 7 with shallow chevron-shape ribs 9 to enhance grip.

The dilator is curved along substantially its entire length. Approximately the first 25 mm of the patient end region 5 is straight but the remainder of the patient end region and the intermediate region 6 is curved with a radius of about 90 mm. The handle region 7 is curved with a similar radius of curvature but in the opposite sense. These two curves give the dilator an overall S shape.

A passage 10 extends along a part only of the length of the dilator. The diameter of the passage 10 varies with the taper of the dilator, being about 9 mm at its widest, rear end in the region of the handle 7 and 2 mm at the patient end tip 4. The wall thickness of the dilator reduces along the patient end region 5 as the dilator tapers to a reduced diameter. One end of the passage 10 opens axially through an opening 11 at the patient end 4. The other end of the passage 10 opens on a side of the dilator through a side opening 12 spaced towards the forward end of the handle region 7. The rear end side opening 12 of the passage 10 is located on the inside or concave side of the handle region 7. The rear end side opening 12 of the passage 10 is provided by a combination of an elongate, longitudinally-extending aperture 13 formed in the tubular component 1 and by a side edge 14 of the plug 2.

The plug 2 is moulded of polyurethane, or similar material, and comprises a rear head 20, a stem 21 and a forward pad 22. The stem 21 has a diameter about one third the internal diameter of the tubular component and is flexible. The plug 2 is inserted into the rear end of the tubular component 1 using a solvent or the like as a lubricant, which also acts to bond the insert in place within the tubular component. Alternatively, the plug could be retained by means of surface formations, such as barbs, or a combination of surface formations and a solvent, adhesive or bond. The pad 22 has a flat forward ramp surface 23, inclined at about 45° to the axis of the dilator, and a rearwardly-extending cylindrical collar 24, which is a close fit within the tubular component 1. The ramp surface 23 is inclined towards the opening 12 and is spaced a short distance forwardly of the rear edge of the opening 12 so that the forward end of the collar projects a short distance across the rear end of the opening and provides the edge 14 referred to above.

The outside of the dilator is coated by dipping along its patient end and intermediate regions 5 and 6 with a hydrophilic coating, to aid insertion in the opening to the trachea.

The tubular component 1 and insert 2 are preferably both moulded in a straight or linear shape, as shown in FIG. 5. After the insert 2 has been inserted into the rear end of the tubular component, the dilator is subsequently bent and retained in the desired shape. It is then subjected to heat treatment followed by cooling to set it in this curved shape. The flexible nature of the stem 21 of the plug 2 ensures that this does not make it difficult to bend the dilator during this stage of manufacture.

The dilator receives a guidewire 30 and guide catheter 31 or similar other guide member extending along its passage 10, with their patient ends emerging from the opening 11 at the patient end 4 of the dilator and with their rear ends emerging from the side opening 12. The rear end of the guidewire 30 and catheter 31 extend rearwardly along the outside of the handle 7.

The dilator is used in the conventional percutaneous tracheostomy procedure. In this, a needle is first inserted through the skin into the trachea and a cannula is inserted through the needle. The needle is them removed leaving the cannula in position. The guidewire 30 is then inserted through the cannula and the cannula is then removed. A predilator is slid along the guidewire 30 to enlarge the opening into the trachea slightly. After removal of the predilator, the guide catheter 31 is slid along the guidewire 30. The rear end of the guide catheter 31 and guidewire 30 are then inserted in the opening 11 at the patient end 4 of the dilator and it is threaded rearwardly along these guide members until they emerge from the side opening 12. The curvature of the patient end 5 and intermediate portion 6 of the dilator are such that guiding catheter 31 and guidewire 30 are naturally directed towards the side on which the opening 12 is located. The ramp surface 23 ensures that the guide members 30 and 31 are directed to the opening 12 even if they are kinked or deformed slightly. The dilator is slid along the guide members 30 and 31 and pushed through the opening into the trachea, expanding it as it is inserted, up to about 38 FR. The guiding catheter 31 has a diameter substantially equal to the diameter of the opening 11 at the tip 4. This, and the thin wall of the dilator at this point ensure a substantially stepless transition between the guide catheter 31 and dilator, thereby facilitating insertion and reducing tissue trauma.

The present construction of the dilator allows it to be used readily in a slightly different way, where the guide member is retained with the dilator against relative movement between them so that both the guide member and the dilator are pushed into the trachea together. This is achieved simply by the user pushing his thumb over the side opening 12 to hold the guide catheter 31 against the edge surface 14 and by holding the guide catheter against the side of the rear of the dilator. This prevents relative movement between the dilator and the guide catheter 31 until thumb pressure is released.

After dilation, the dilator is removed and a tracheostomy tube mounted on an introducer is slid into the trachea, through the expanded opening in the usual way.

The curved shape of the dilator handle 7 gives it ergonomic advantages and thereby overcomes the problem of how to enable the user to apply a relatively high insertion force but in a controlled manner. The dilator could be held in different ways. Typically, it might be held like a spoon, between thumb and forefinger, for the initial sliding along the guidewire and penetration of the skin surface. Thereafter, when additional force is required, the user can shift his grip easily to hold the dilator like a trowel where the handle region 7 lies across the palm and is held against it by the little finger, ring finger and forefinger. The patient end region 5 of the dilator emerges from the hand between the thumb and the second joint of the forefinger and curves in the direction of the thumb. The thumb and forefinger provide the guidance and the other three finger provide the force. In this grip, the curve of the handle region 7 follows the shape of the palm grip allowing for a secure grip, which enables a well-controlled force to be applied.

Dilators according to the present invention may be used to expand a tracheostomy at various locations from the cricothyroid region to locations caudally along the trachea.

The dilator need not be formed in two parts as described above. Instead, the handle portion 7 could be moulded with an integral internal ramp. A location groove could be formed extending longitudinally along the outside of the handle portion to help retain the guide member with the outside of the dilator. Alternatively, some other formation could be used to guide or retain a guide member with the dilator.

The invention claimed is:

1. A tracheostomy dilator comprising a patient end region that is curved to one side and tapers to a reduced diameter at its patient end, the patient end region being adapted for insertion through a tracheostomy to expand the tracheostomy, a handle region towards a rear end of the dilator opposite the patient end region, and a passage for receiving a guide member extending within the dilator from its patient end such that the dilator can be slid forwardly through the tracheostomy along the guide member, characterized in that the passage opens on a side of the dilator through an opening forwardly of its rear end.

2. A dilator according to claim 1, characterized in that the passage opens within the handle region.

3. A dilator according to claim 1, characterized in that the handle region is curved in an opposite sense to one side from the patient end region forming a smooth continuous curve with the patient end region.

4. A dilator according to claim 3, characterized in that the passage opens on an inside curve of the handle region.

5. A dilator according to claim 1, characterized in that the handle region includes an insert with a ramp surface arranged to direct a guide member inserted in the dilator.

* * * * *